(12) United States Patent
Bhatia et al.

(10) Patent No.: US 7,479,289 B2
(45) Date of Patent: Jan. 20, 2009

(54) STABLE CLEANSER COMPOSITIONS CONTAINING SULFUR

(75) Inventors: Kuljit S. Bhatia, Chandler, AZ (US); Bhiku G. Patel, Chandler, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

(21) Appl. No.: 10/884,296

(22) Filed: Jul. 2, 2004

(65) Prior Publication Data

US 2006/0003034 A1 Jan. 5, 2006

(51) Int. Cl.
*A01N 59/02* (2006.01)
*A61K 33/04* (2006.01)
(52) U.S. Cl. ........................... 424/703; 514/859
(58) Field of Classification Search ............... 424/703; 514/859
See application file for complete search history.

(56) References Cited

U.S. PATENT DOCUMENTS

| | | | |
|---|---|---|---|
| 3,634,264 A | 1/1972 | Pence | |
| 4,388,301 A | 6/1983 | Klein | |
| 4,545,990 A | 10/1985 | Le Foyer de Costil et al. | |
| 4,587,123 A | 5/1986 | Price | |
| 4,735,935 A | 4/1988 | McAnalley | |
| 4,752,472 A | 6/1988 | Kligman | |
| 4,803,228 A | 2/1989 | Jacquet et al. | |
| 4,891,228 A | 1/1990 | Thaman et al. | |
| 4,906,617 A | 3/1990 | Jacquet et al. | |
| 4,917,891 A | 4/1990 | Kaufmann et al. | |
| 4,960,772 A | 10/1990 | Sebag et al. | |
| 4,978,695 A | 12/1990 | Hoshino et al. | |
| 5,019,567 A | 5/1991 | Philippe et al. | |
| 5,254,109 A | 10/1993 | Smith et al. | |
| 5,344,971 A | 9/1994 | Dedieu et al. | |
| 5,368,581 A | 11/1994 | Smith et al. | |
| 5,387,363 A | 2/1995 | Distaso | |
| 5,409,706 A | 4/1995 | Ramirez et al. | |
| 5,417,674 A | 5/1995 | Smith et al. | |
| 5,470,884 A | 11/1995 | Corless et al. | |
| 5,562,642 A | 10/1996 | Smith et al. | |
| 5,632,996 A | 5/1997 | Ramirez et al. | |
| 5,648,389 A | 7/1997 | Gans et al. | |
| 5,660,839 A | 8/1997 | Allec et al. | |
| 5,690,946 A | 11/1997 | Koulbanis et al. | |
| 5,756,107 A | 5/1998 | Hahn et al. | |
| 5,756,119 A | 5/1998 | Deckner et al. | |
| 5,767,098 A | 6/1998 | Klein et al. | |
| 5,821,209 A | 10/1998 | Distaso et al. | |
| 5,821,237 A | 10/1998 | Bissett et al. | |
| 5,849,834 A | 12/1998 | Matsuzaki et al. | |
| 5,874,074 A | 2/1999 | Smith | |
| 5,880,079 A | 3/1999 | Polotti et al. | |
| 5,951,991 A | 9/1999 | Wagner et al. | |
| 5,958,436 A | 9/1999 | Hahn et al. | |
| 5,997,885 A | 12/1999 | Koulbanis et al. | |
| 6,001,380 A | 12/1999 | Smith et al. | |
| 6,017,549 A | 1/2000 | Knight et al. | |
| 6,113,921 A | 9/2000 | Friedman et al. | |
| 6,149,926 A | 11/2000 | Venkitaraman et al. | |
| 6,153,208 A | 11/2000 | McAtee et al. | |
| 6,183,766 B1 | 2/2001 | Sine et al. | |
| 6,338,855 B1 | 1/2002 | Albacarys et al. | |
| 6,413,536 B1 | 7/2002 | Gibson et al. | |
| 6,429,231 B1 | 8/2002 | Bhagwat et al. | |
| 6,455,076 B1 | 9/2002 | Hahn et al. | |
| 6,462,025 B2 | 10/2002 | Vishnupad | |
| 6,469,227 B1 | 10/2002 | Cooke et al. | |
| 6,784,145 B2 | 8/2004 | Delambre et al. | |
| 6,861,397 B2 | 3/2005 | Seitz et al. | |
| 6,977,081 B1 | 12/2005 | Rood | |
| 2002/0086039 A1* | 7/2002 | Lee et al. | ............... 424/401 |
| 2002/0164381 A1* | 11/2002 | Shacknai et al. | ............ 424/703 |
| 2003/0031727 A1 | 2/2003 | Hahn et al. | |
| 2005/0025817 A1 | 2/2005 | Bhatia et al. | |
| 2005/0232978 A1 | 10/2005 | Patel et al. | |

FOREIGN PATENT DOCUMENTS

| | | |
|---|---|---|
| EP | 0 576 287 A1 | 12/1993 |
| JP | 03-002124 | 1/1991 |
| WO | WO 82/04393 | 12/1982 |
| WO | WO 92/05764 | 4/1992 |
| WO | WO 98/04241 | 2/1998 |

(Continued)

OTHER PUBLICATIONS

Physicians's Desk Reference, 2004, 58th edition, published Nov. 2003, Thomas Healthcare, pp. 1906-1907.

(Continued)

*Primary Examiner*—Yong Chong
(74) *Attorney, Agent, or Firm*—William J. McNichol, Jr.; Maryellen Feehery Hank; Reed Smith LLP (57) ABSTRACT

The present invention is a composition, preferably a cleanser, comprising sulfur, sodium sulfacetamide and at least one emulsifier with a low HLB number. These compositions are stable and may include moisturizers and humectants. Use of these compositions include treatments for acne rosacea, acne vulgaris and other skin disorders.

2 Claims, 8 Drawing Sheets
(8 of 8 Drawing Sheet(s) Filed in Color)

FOREIGN PATENT DOCUMENTS

| WO | WO 98/47466 | 10/1998 |
|----|-------------|---------|
| WO | WO 99/24003 | 5/1999  |

OTHER PUBLICATIONS

Harry, R.G., "Harry's Cosmeticology", pp. 558-561, 6th edition (1973).

Bonnar, et al., "The Demodex Mite Population in Rosacea", Journal of the American Academy of Dermatology, vol. 28, No. 3, pp. 443-448, Mar. 1993.

Diaz-Perez et al., "Demodex mites in Rosacea" and "Reply", Journal of the American Academy of Dermatology, vol. 30, No. 5, Part 1, pp. 812-813, May 1994.

"Dermatology in General Medicine", 5th edition, CD-ROM, Chapter 74, (1999).

Lin et al., "Sulfur Revisited", Journal of the American Academy of Dermatology, vol. 18, No. 3, pp. 553-558, Mar. 1998.

Maibach, et al., "Sulfur Revisited" and "Reply", Journal of the American Academy of Dermatology, vol. 23, No. 1, pp. 154-156, Jul. 1990.

Sojka et al., "New Polymer Technology For Skin Oil Adsorbers and Controlled Release", Allured's Cosmetics & Toiletries Magazine, vol. 114, No. 3, pp. 83-86 and 88, Mar. 1999.

Database WPI Section Ch. Week 1986 Derwent Publications Ltd. London, GB; XP002245540 & RO 87 009 A (Intr Prod Cosmetice Farmec) May 30, 1985 (abstract).

The Merck Manual, Seventeenth Edition (1999), pp. 811-814.

Marks, "Histopathology of Rosacea", Arch. Derm., vol. 100, pp. 683-691, Dec. 1969.

Dominey et al., "Papulondular demodicidosis associated with acquired immunodeficiency syndrome," Journal of the American Academy of Dermatology, Feb. 1989, vol. 20, pp. 197-201.

Ecker, et al., "Demodex Granuloma," Arch Dermatol; Mar. 1979, vol. 115, pp. 343-344.

Schewach-Miller et al., "Granulomatous rosacea," Journal of the American Academy of Dermatology, Jun. 1988, vol. 18, No. 6, pp. 1363-1362.

Alexander Jo'D., "Hair follicle mites in men," In Arthropods and Human Skin, Berlin: Sreipenger-Verlag, 1984.

Merck Index pp. 697-698, 1288-1289 (1983).

Ayres et al. "Demodectic Eruptions (Demodicidosis) in the Human," Arch. Derm., vol. 83, May 1961, pp. 816-827.

Milks, Howard Jay, "Sulfur Compounds" Practical Veterinary Pharmacology, Materia Medica and Therapeutics, 1949, Sixth Edition, pp. 552-560.

Griffin, Calculation of HLB Values of Non-Ionic Surfactants, *The Journal Of The Society Of Cosmetic Chemists*, vol. V, No. 4, Dec. 1954, p. 249-256.

Griffin, Classification of Surface-Active Agents By "HLB", *The Journal Of The Society Of Cosmetic Chemists*, vol. I, No. 5, Dec. 1949, p. 311-326.

Physicians' Desk Reference 57th Edition. Montvale, NJ(2003); Plexion, pp. 1926-1927.

Waller, T. "Aloe Vera in Personal Care Products," *Cosmetic & Toiletries*, (Aug. 1992).

Moroni P., "Aloe in Cosmetic Formulations," *Cosmetic Technology* (Sep. 1982).

"Aloe Vera Gel," Handbook of Non-Prescription Drugs, American Pharmaceutical Ass'n., Washington, D.C., p. 707 (1996).

"Allantoin," Handbook of Non-Prescription Drugs, American Pharmaceutical Ass'n., Washington, D.C., pp. 548- and 640 (1996).

Jappe, U., "Pathological Mechanisms of Acne with Special Emphasis on Propionibacterium acnes and related Therapy," *Acta Derm Venereol*,; 83 pp. 241-248 (2003).

"α-Bisabolo" *Merck Index*, Merck & Co., Twelve Edition, pp. 208-209 (1996).

Basta-Juzbasic, A., "Demodex Folliculorum in Development of Dermatitis Rosaceiformis Steroidica and Rosacea-Related Diseases," *Clinics in Dermatology*, 20 pp. 135-140 (2002).

"Allantoin" *Merck Index*, Merck & Co., Twelve Edition, p. 48 (1996).

Manna, S, "Determination of the Position of the *O*-Acetyl Group in a β-(1 → 4)-Mannan (Acemannan) from Aloe barbardensis Miller," *Carbohydrate Research*, 241, pp. 317-319 (1993).

CTFA Cosmetic Ingredient Handbook, pp. 64-65, 78-85 (1988).

International Cosmetic Ingredient Dictionary and Handbook, pp. 65, 69-74, 185, 2929-2938 (2002).

Steinberg, D., "U.S. Regulations Update:FDA Issues Final Monograph for Skin Protectants," *Cosmetics & Toiletries*, 118(8) pp. 20-28 (Aug. 2003).

Martindale, 32d Edition, pp. 11 (1999).

\* cited by examiner

Fig 2a

STABLE CLEANSER COMPOSITIONS CONTAINING SULFUR

FIELD OF THE INVENTION

The present invention relates to stable cleanser compositions useful in the treatment and prevention of acne vulgaris, acne rosacea, other dermatological disorders and their manifestations in the skin. Cleansers are particularly attractive as treatments for these disorders, especially if the active ingredients may be sufficiently delivered to the skin in the short time a cleanser contacts the skin. Patient compliance may be higher than usual because only a cleanser is required as opposed to two products, a cleanser and then a composition with the active ingredient.

BACKGROUND OF THE INVENTION

The use of sulfur in dermatological products has been known for many years. The sulfur may be useful on dermatological disorders such as acne vulgaris, acne rosacea, mite infestations and other conditions. Sodium sulfacetamide is also often used in combination with sulfur for the treatment and/or prevention of such dermatological disorders. However, there are several problems with sulfur formulations in the prior art.

First, sulfur and sodium sulfacetamide may degrade into malodorous components, such as sulfanilamide. Chemical and physical stability for sulfur and sodium sulfacetamide compositions has been difficult to achieve. Many sulfur compositions degrade, turn color and become malodorous in a relatively short time, which is undesirable to consumers.

Patients frequently use sulfur and sodium sulfacetamide compositions on the face and other skin. In order to promote compliance, it is desirable to have non-malodorous and aesthetically pleasing compositions.

Sulfur and sodium sulfacetamide compositions in the art have employed gums, clays, silicates and other sorptive materials in order to promote stability of the sulfur and sodium sulfacetamide. However, the stability provided by these sorptive materials is limited and often not conducive to cleanser compositions. In certain embodiments without limitation, the present invention does not comprise gums, clays, silicates and other sorptive materials.

Sorptive materials are defined to include those materials which, when applied topically to the skin, absorb irritants, including but not limited to sweat, sebum, oil and dirt, from the skin.

Sulfur and sodium sulfacetamide compositions in the art frequently use emulsifiers with HLB ("Hydrophilic Lipophilic Balance") numbers of around 30 or combined HLB numbers of about 30 or higher. However, chemical and physical stability appear to suffer in these compositions.

HLB Numbers

An HLB number referred to in this specification is calculated in the manner developed by William Griffin and used by ICI Americas, Inc. ("ICI"). It is well-known in the art and conventionally calculated and published. See, Griffin, W. C. "Classification of Surface-Active Agents by HLB," J. Soc. Cosmet. Chem. 1, 311-326 (1949); and Griffin, W. C. "Calculation of HLB Values of Non-Ionic Surfactants," J. Soc. Cosmet. Chem. 5, 249-256 (1954) (incorporated herein by reference). ICI has published numerous reference materials regarding the HLB number.

The HLB number is an indication of the hydrophilic portion of an emulsifier molecule. The HLB number indicates the polarity of the molecules in a 1-20 range, and the number increases with increasing hydrophilicity. HLB numbers are usually calculated or obtained experimentally for nonionic surfactants. However, HLB numbers are often assigned up to 40 for ionic surfactants. These numbers over 20 are relative or comparative numbers, which are not based on strict mathematical formulas, but are conventionally known and used. If a nonionic emulsifier were 100% hydrophilic, the HLB number would be 20, because the factor ⅕ is used (e.g. ⅕ of 100). An emulsifier that is lipophilic has a HLB number of below about 9 and one that is hydrophilic has a HLB number of above about 11. Those in the range of about 9-about 11 are indeterminate. ICI publishes the HLB number of many of its emulsifiers, and the other are calculable using the ICI method, which is known in the art. ICI also set forth the following information regarding the uses of emulsifiers.

TABLE 1

| HLB Range | Use |
|---|---|
| 4-6 | Water/Oil Emulsifiers |
| 7-9 | Wetting Agent |
| 8-18 | O/W Emulsifiers |
| 13-15 | Detergents |
| 10-18 | Solubilizers |

When two or more emulsifiers are combined, the resulting combined HLB number is calculated by adding (the percentage of emulsifier(1) multiplied by HLB(1)) and (the percentage of emulsifier(2) multiplied by HLB(2)). This can be calculated for any number of emulsifiers which are combined.

HLB numbers can help predict what are the appropriate emulsifiers to use in a particular instance. The chemical type of the emulsifier also plays an important role in the most effective emulsifiers as is understood by one of ordinary skill in the art. In fact, the most stable emulsifier systems usually consist of combinations of two or more emulsifiers, a portion with lipophilic tendencies and a portion with hydrophilic tendencies.

ICI also provides the following guidance on dispersibility in water.

TABLE 2

| HLB by Dispersibility | HLB Range |
|---|---|
| No dispersibility in water | 1-4 |
| Poor dispersion | 3-6 |
| Milky dispersion after vigorous agitation | 6-8 |
| Stable milky dispersion | 8-10 |
| Translucent to clear dispersion | 10-13 |
| Clear solution | 13+ |

Preparing stable emulsions, as is known to those of ordinary skill in the art, is an inexact and time-consuming process. To date, sulfur and sodium sulfacetamide compositions, which are emulsions, and particularly cleansers, have shown a tendency to be unstable, physically and chemically. The present invention achieves a surprising stability for such compositions, along with the additional benefit of being aesthetically pleasing and dermatologically desirable.

SUMMARY OF THE INVENTION

The present invention includes a stable composition comprising sulfur, sodium sulfacetamide, and at least one emulsifier, which has a low HLB number. A low HLB number is less than about 8, more preferably less than about 5, and most preferably about 4.7 and below. The preferred amount of sulfur is up to about 5% by weight (all percentages in the specification are by weight unless otherwise noted), most preferably about 5% with appropriate overage amounts to satisfy FDA requirements of a composition labeled 5% sulfur. The preferred amount of sodium sulfacetamide is up to about 10%, most preferably about 10% with appropriate overage amounts to satisfy FDA requirements of a composition labeled 10% sodium sulfacetamide. The pH of the composition is preferably about 5.0 to about 8.0, and more preferably about 7.0.

Emulsifiers are characterized according to the balance of the hydrophilic and lipophilic parts. In this specification, the term emulsifiers may also include surfactants, which behave as emulsifiers but may not be formally called emulsifiers. In the present invention, at least one emulsifier must have a low HLB number. "High" HLB number means about 35 to about 40.

Emulsifiers, which have low HLB numbers and may be suitable to this composition include but are not limited to sorbitan monooleate (sold under the name Crill 4), Brij 72, Span 60, Span 80, sodium methyl oleyltaurate, disodium oleamido mea sulfosuccinate, PEG-55 propylene glycol oleate, sodium cocoyl isethionate, cetyl alcohol, stearyl alcohol, sodium lauryl sulfoacetate, disodium laureth sulfosuccinate, sorbitan monooleate, glyceryl stearate, PEG-100 stearate. One of ordinary skill in the art would identify and recognize such emulsifiers (or surfactants behaving as emulsifiers) with low HLB numbers and such emulsifiers (or surfactants behaving as emulsifiers) are published for example in McCutcheon's Emulsifiers & Detergents, 2003 North American Edition, pp. 238-242 (incorporated herein by reference). The emulsifier with low HLB number may be present in the invention in the range of less than about 8; preferably less than about 5; and most preferably about 4.7 and below. In certain embodiments, combinations of emulsifiers with a combined low HLB number may be present in the invention in the range of about 2 to about 10.

In certain embodiments, the composition comprises sulfur, sulfur-containing ingredient and at least one emulsifier, which has a low HLB number.

"Sulfur-containing ingredient" as used herein means any composition that contains organic or inorganic sulfides, inorganic sulfites, organic or inorganic mercaptans, or any other which may be used in a topical skin application to treat dermatological disorders (such as, without limitation, acne rosacea, acne vulgaris or seborrheic dermatitis), including but not limited to cationic sulfur compounds, such as selenium sulfide, potassium sulfide, poly-potassium sulfide, poly-calcium polysulfide, $H_2S$, sulfuric acid, bisulfides, sulfur dioxide, thiols, organic salts, sodium sulfacetamide, or combinations thereof, and excludes sulfur, as defined below.

Sulfur (or elemental sulfur) is a chemically active element and there are several forms of elemental sulfur. Forms of elemental sulfur suitable for use in the present invention are those forms of elemental sulfur that are known to be useful in dermatological compositions, including but not limited to, colloidal, coated, enrobed, entrapped, fumed, precipitated, washed and sublimed sulfur, milk of sulfur and flowers of sulfur. The preferred form of sulfur for use in the present invention is precipitated sulfur.

Inorganic sulfides suitable for use in connection with the present invention are those inorganic sulfides known to be useful in dermatological compositions and include, but are not limited to, selenium sulfide, sodium thiosulfate as well as those inorganic sulfides having the formula: RS, RSH, $R_2S$, RSSR, or RSSH, wherein R is an inorganic element that can bind ionically or covalently with sulfur.

Organic sulfides suitable for use in connection with the present invention are those organic sulfides known to be useful in dermatological compositions and include, but are not limited to, those organic sulfides having the formula: RS, R2S, RSH, R'SSR' , or R'SSH, wherein R' is an organic compound and its salts that can bind ionically or covalently with sulfur. Exemplary organic sulfides include, but are not limited to sodium thioglycolate (sodium mercaptoacetic acid), and gluathione.

Inorganic sulfites suitable for use in the present invention are those inorganic sulfites known to be useful in dermatological compositions, including but not limited to, sulfites and metabisulfites.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF SPECIFIC EMBODIMENTS

In certain embodiments, the composition comprises sulfur, a sulfur-containing ingredient, at least one emulsifier with a high HLB number and at least one emulsifier with a low HLB number, wherein the combined HLB number is low. In certain embodiments, the composition comprises sulfur, a sulfur-containing ingredient, at least one emulsifier with a high HLB number and at least one emulsifier with a low HLB number.

An embodiment of the invention is a composition comprising the following:

TABLE 3

| Ingredient | Weight % |
| --- | --- |
| Water | 47.66 |
| Glycerin 99% | 2.00 |
| Methyl Paraben | 0.15 |
| Propyl Paraben | 0.15 |
| Allantoin | 0.10 |
| Edetate Sodium | 0.20 |
| Sodium Methyl Oleyltaurate (Tauranol MS) | 9.15 |
| Disodium Oleamido MEA Sulfosuccinate | 3.85 |

TABLE 3-continued

| Ingredient | Weight % |
|---|---|
| (Mackanate OM) | |
| PEG-55 Propylene Glycol Oleate (Antil 141 Liquid) | 1.35 |
| Sodium Cocoyl Isethionate (Tauranol I-78C) | 8.50 |
| Sodium Lauryl Sulfoacetate (and) Disodium Laureth Sulfosuccinate (Stepan-Mild LSB) | 4.50 |
| Cetyl Alcohol (Crodacol C95) | 2.00 |
| Stearyl Alcohol (Crodacol S95) | 1.50 |
| Sorbitan Monooleate (Crill 4) | 2.00 |
| Glyceryl Stearate & PEG 100 Stearate (Arlacel 165) | 2.00 |
| Butylated Hydroxytoluene ("BHT") | 0.15 |
| Alpha-Bisabolol natural | 0.10 |
| Sulfur, precipitated | 5.00 |
| PEG-150 Pentaerythrityl Tetrastearate | 0.15 |
| Aloe Vera 1X Decolorized Gel | 0.10 |
| Sodium Thiosulfate | 0.15 |
| Sulfacetamide Sodium | 11.24 |
| Fragrance 27160 | 0.10 |

Another embodiment of the invention is a composition comprising the following:

TABLE 4

| Ingredient | Weight % |
|---|---|
| Water | 49.16 |
| Glycerin 99% | 2.00 |
| Methyl Paraben | 0.15 |
| Propyl Paraben | 0.05 |
| Allantoin | 0.10 |
| Edetate Sodium | 0.20 |
| Sodium Methyl Oleyltaurate (Tauranol MS) | 9.15 |
| Disodium Oleamido MEA Sulfosuccinate (Mackanate OM) | 3.85 |
| PEG-55 Propylene Glycol Oleate (Antil 141 Liquid) | 1.35 |
| Sodium Cocoyl Isethionate (Tauranol I-78C) | 6.50 |
| Sodium Lauryl Sulfoacetate (and) Disodium Laureth Sulfosuccinate (Stepan-Mild LSB) | 4.50 |
| Cetyl Alcohol (Crodacol C95) | 1.00 |
| Stearyl Alcohol (Crodacol S95) | 1.00 |
| Sorbitan Monooleate (Crill 4) | 2.00 |
| Glyceryl Stearate & PEG 100 Stearate (Arlacel 165) | 2.00 |
| Butylated Hydroxytoluene ("BHT") | 0.15 |
| Alpha-Bisabolol natural | 0.10 |
| Sulfur, precipitated | 5.00 |
| PEG-150 Pentaerythrityl Tetrastearate | 0.15 |
| Aloe Vera 1X Decolorized Gel | 0.10 |
| Sodium Thiosulfate | 0.15 |
| Sulfacetamide Sodium | 11.24 |
| Fragrance 27160 | 0.10 |

Another embodiment of the invention is a composition comprising the following:

TABLE 5

| Ingredient | Weight % |
|---|---|
| Water (preferably purified water) | 48.66 |
| Glycerin USP | 2.00 |
| Methyl Paraben NF | 0.15 |
| Propyl Paraben NF | 0.05 |
| Allantoin | 0.10 |
| Sodium Methyl Oleyltaurate (Tauranol MS) | 9.15 |
| Disodium Oleamido MEA Sulfosuccinate (Mackanate OM) | 3.85 |
| Propylene Glycol (and) PEG-55 Propylene Glycol Oleate (Antil 141 Liquid) | 1.35 |
| Sodium Cocoyl Isethionate (Tauranol I-78C) | 6.50 |
| Sodium Lauryl Sulfoacetate (and) Disodium Laureth Sulfosuccinate (Stepan-Mild LSB) | 4.50 |
| Cetyl Alcohol (Crodacol C95) | 1.00 |
| Stearyl Alcohol (Crodacol S95) | 1.50 |
| Sorbitan Monooleate (Crill 4) | 2.00 |
| Glyceryl Stearate & PEG 100 Stearate (Arlacel 165) | 2.00 |
| Butylated Hydroxytoluene ("BHT") | 0.15 |
| Alpha-Bisabolol natural | 0.10 |
| Sulfur, precipitated | 5.00 |
| Edetate Disodium | 0.20 |
| PEG-150 Pentaerythrityl Tetrastearate (Crothix) | 0.15 |
| Aloe Vera 1X Decolorized Gel IX | 0.10 |
| Sodium Thiosulfate | 0.15 |
| Sulfacetamide Sodium | 11.24 |
| Fragrance | 0.10 |
| Total Percent | 100% |
| *Water, USP (as a pharmaceutical processing aid) | 3.00 (additional) |

*An additional 3% water is added as a pharmaceutical processing aid after all the other components total 100%.

In the present invention, sulfur and sodium sulfacetamide compositions are formulated in stable, non-malodorous compositions, which are preferably cleansers. The composition may be in the form of emulsions, suspensions, lotions, creams, and gels, preferably emulsions or suspensions.

One of ordinary skill in the art would understand that the viscosity of the embodiments may be modified for delivery and cosmetic reasons without altering the invention. In this specification, unless otherwise specified, the viscosity is measured on a Brookfield RVTD viscometer at about 25° C.±1° C. for 1 minute with the spindle set for 20 rpm (spindle set RV). It is preferred to measure the viscosity at about 24 hours after the composition was made. The preferred viscosity is about 5000 to about 70,000 cps, more preferably about 35,000 cps to about 45,000 cps, more preferably about 25,000 to about 35,000 cps, most preferably about 30,000 cps. Another preferred viscosity is about 26,000 cps. Another preferred viscosity is about 41,000 cps.

Viscosity Measuring Technique

The compositions of the present invention may be tested for viscosity in the following manner. All viscosities in this specification are measured in this manner unless otherwise noted. A Brookfield viscometer model No. RVTD with RV spindle set. The spindle used should be one in which the reading is mid-range for good accuracy.

In this viscosity testing, the following procedure should be used. Dispense 140 ml of Standard into a 150 ml beaker. The standard should be tested twice, one standard below the expected sample viscosity and one above. The temperature of the standard should be 25 C+−1 C. Use a water bath or other appropriate device to maintain constant temperature during measurement. Lower the viscometer head with spindle attached slowly into standard until the surface of the standard is located within the groove above the spindle disk. Zero the viscometer readout. Adjust the spindle speed to 20 rpm. Turn on the viscometer and allow it to rotate for one minute. Take a reading, and multiply the reading by the chart multiplication factor for the spindle. The resulting reading should be the same as the standard used within +/−10%. Then, the sample of the invention is equilibrated to 25 C+/−1 C. The amount of sample and the size of the sample container should be such that the test spindle can be placed into the sample container with no obstruction. The temperature is maintained at 25C +/−1 C. Lower the viscometer head with spindle attached slowly into sample until the surface is located within the groove above the spindle disk. Zero the viscometer readout. Adjust the spindle speed to 20 rpm. Turn on the viscometer and allow it to rotate for one (1) minute. Take the reading and calculate with the chart multiplication factor.

In a preferred embodiment, at least one emulsifier with a low HLB number (e.g., without limitation, Crill 4 NF or sodium monoleate with HLB=about 4.7) is present to help balance at least one emulsifier with high HLB number and help stabilize the emulsion.

Preferred emulsifiers (or surfactants which may behave as emulsifiers) include, but are not limited to, sodium methyl oleyltaurate, disodium oleamido mea sulfosuccinate, PEG-55 propylene glycol oleate, sodium cocoyl isethionate, cetyl alcohol, stearyl alcohol, sorbitan monooleate, glyceryl stearate (and) PEG 100 stearate, and sodium lauryl sulfoacetate (and) disodium laureth sulfosuccinate.

Additionally, it may be desirable to have one or more humectant in the composition to hydrate the skin. Humectants may include those known to those of ordinary skill in the art to hydrate the skin, preferably, without limitation, glycerin.

Further, it may be desirable to have one or more moisturizer in the composition to moisturize the skin. Skin subject to these disorders may be sensitive and dry, and therefore moisturizers may be beneficial. Moisturizers may include those known to those of ordinary skill in the art to moisturize the skin, preferably, without limitation, allantoin, bisabolol (preferably alpha-bisabolol natural), and aloe vera gel (preferably aloe vera 1X decolorized gel).

In some embodiments, preservatives, fragrances and coloring may be added. Preservatives may include those known to those of ordinary skill in the art and preferably, without limitation, methyl paraben, propyl paraben, and butylated hydroxytoluene ("BHT").

EXAMPLE 1

One batch of the present invention as described in Table 3 was prepared and tested for viscosity and stability.

The viscosity measurements were taken as described in the specification. The top of the batch measured about 7150 cps, middle about 7850 cps and bottom about 6800 cps.

As noted above, sulfanilamide is the result of degradation reactions within the composition, and a sufficient amount of sulfanilamide causes malodor in a composition. As seen below, the composition did not degrade.

The composition was divided into three sub-batches. One sub-batch was stored in 55 gallon drums, which were flushed with nitrogen and after filling, packaged with a nitrogen blanket. Another sub-batch was packaged in tubes, which had been flushed with nitrogen. A third sub-batch, under a nitrogen blanket, was deposited on a non-woven cloth and sealed in a package.

The batches were tested initially and after being stored at 25° C. for 1 month, the tubes and cloths were also tested after being stored at 40° C. for 1 month, and the cloth was also tested after being stored at 40° C. for 1 month. Additionally, the compositions were visually observed for discoloration, which is also a sign of degradation, and is not cosmetically acceptable.

TABLE 6

(bulk tested)

|  | Initial | 1 Month 25° C. |
|---|---|---|
| Sulfacetamide (% LC) | 106.1 | 106.5 |
| % RSD (n = 3) | 0.1 | 0.3 |
| Sulfanilamide (% w/w) | 0.29 | 0.91 |
| % RSD (n = 3) | 2.00 | 1.04 |
| Sulfur(avg % LC) | 102.9 | 101.7 |
| % RSD (n = 3) | 0.3 | 0.7 |
| pH | 7.1 | 6.9 |
| Appearance | Light yellow lotion, No visible separation of layers | Light yellow lotion, No visible separation of layers |

% RSD means percent relative standard deviation. n=3 means that three cloths were tested. % LC means percent of amount of the ingredient to be claimed on the label of an approved FDA product (for example, if the label claimed 5% sulfur and the product had 5% sulfur, % LC would be 100%). Label claims in this specification were assumed to be 5% sulfur and 10% sodium sulfacetamide for these type of calculations.

TABLE 7

(tubes tested)

|  | Initial | 1 Month 25° C. | 1 Month 40° C. |
|---|---|---|---|
| Sulfacetamide (% LC) | 105.5 | 105.2 | 102.7 |
| % RSD (n = 3) | 0.6 | 1.4 | 1.4 |
| Sulfanilamide (% w/w) | 0.53 | 0.94 | 1.90 |
| % RSD (n = 3) | 3.03 | 1.05 | 1.69 |
| Sulfur (avg % LC) | 102.8 | 102.7 | 102.2 |
| % RSD (n = 3) | 0.3 | 3.0 | 1.6 |
| pH | 7.1 | 6.9 | 6.9 |
| Appearance | Light yellow lotion, No visible separation of layers | Light yellow lotion, No visible separation of layers | Light yellow lotion, No visible separation of layers |

TABLE 8

(cloth tested)

|  | Initial | 1 Month 25° C. | 1 Month 40° C. | 2 Month 25° C. | 2 Month 40° C. |
|---|---|---|---|---|---|
| Sulfacetamide (mg/cloth) | 422.6 | 419.2 | 408.0 | 411.5 | 379.0 |
| % RSD (n = 3) | 5.4 | 9.7 | 5.1 | 6.5 | 2.9 |

TABLE 8-continued

| | | (cloth tested) | | | |
|---|---|---|---|---|---|
| | Initial | 1 Month 25° C. | 1 Month 40° C. | 2 Month 25° C. | 2 Month 40° C. |
| Sulfanilamide (% w/w) | 0.69 | 1.11 | 2.74 | 1.68 | 5.46 |
| % RSD (n = 3) | 3.02 | 1.75 | 1.53 | 10.84 | 10.3 |
| Sulfur (mg/cloth) | 201.9 | 208.4 | 207.5 | 203.3 | 194.5 |
| % RSD (n = 3) | 4.4 | 10.4 | 6.9 | 8.49 | 3.76 |
| Appearance | Yellow cloth No discoloration | Yellow cloth No discoloration | Yellow cloth No discoloration | Yellow cloth No discoloration | Yellow cloth No discoloration |

EXAMPLE 2

Additionally, the composition as set forth in Table 3 was prepared and 0.15% fluorescein sodium was added. Then, human skin (the cheek adjacent to the nose and the back of the hand) and cloth were both moistened with water. The cloth with the composition was applied and the composition was allowed to remain for a few minutes. Then, the skin was rinsed off and patted dry.

FIGS. 1a, 1b, 2a, and 2b are all photos of the cheek skin adjacent to the nose. FIGS. 3a, 3b, 4a, and 4b are all photos of the upper side (or back) of the hand.

Figure 1A:
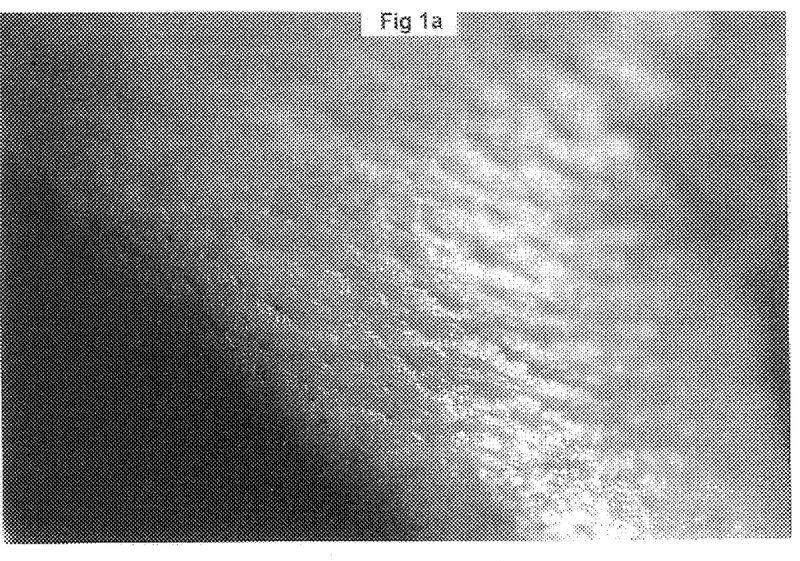
FIG. 1a depicts human skin before cleansing with the present invention.
Figure 1B:
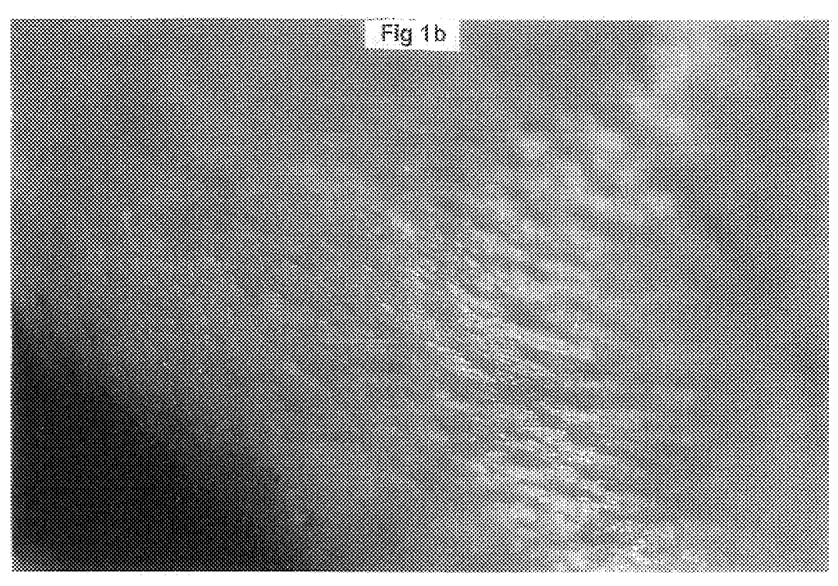
FIG. 1b depicts human skin after cleansing with the present invention.
Figure 2A:
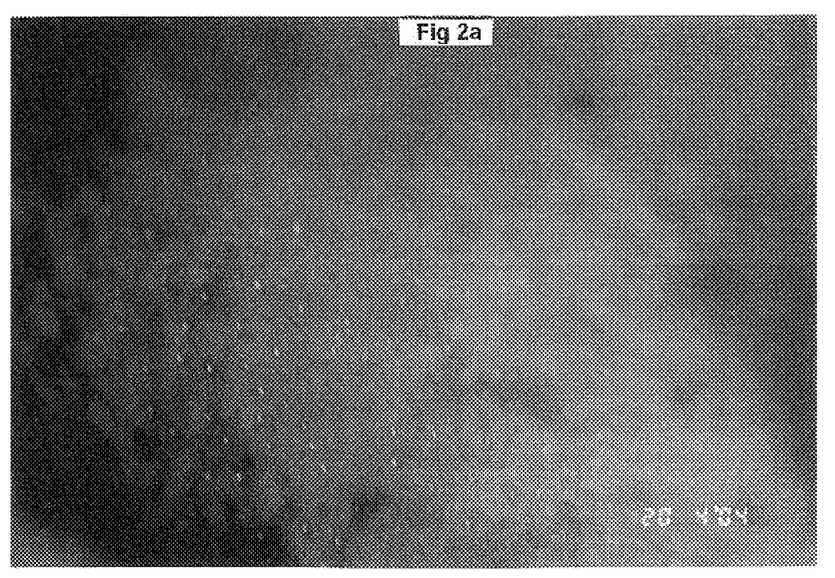
FIG. 2a depicts the same human skin before cleansing as FIG. 1a, but FIG. 2a was photographed under ultraviolet light.
Figure 2B:
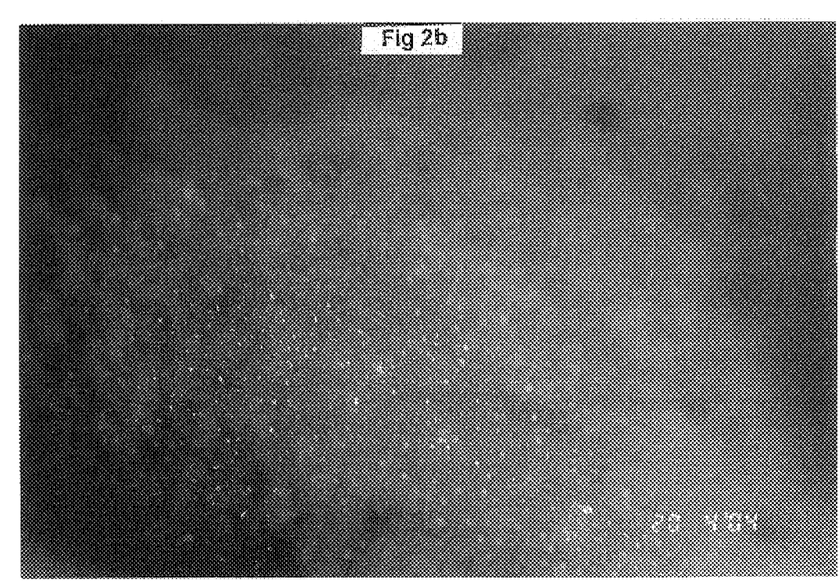
FIG. 2b depicts the same human skin after cleansing as FIG. 1b, but FIG. 2b was photographed under ultraviolet light.

As can be seen in the "before cleansing" photos of FIGS. 1a and 2a, there are blackheads on the lower left side. In FIG. 2a, the small whitish dots are probably coming from the sebum at the opening of the sebaceous follicle (the natural fluorescence is produced by action of P. acnes on the sebum). After cleansing, the same skin area has no blackheads (FIG. 1b), indicating excellent cleansing. FIG. 2b shows numerous yellow dots, which are Fluorescein added to track the presence of the composition. These dots show the deposition and retention of the cleanser within the skin surface and pilosebaceous openings after rinsing.

Figure 3A:
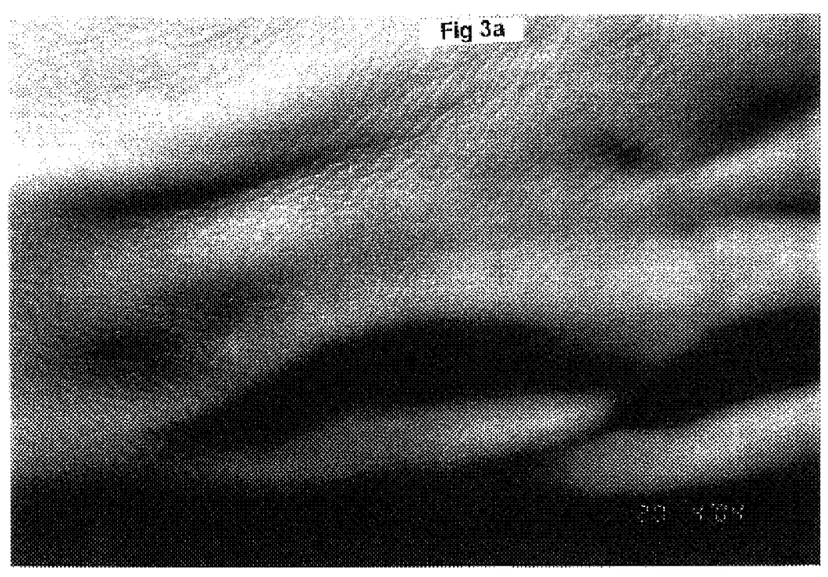
FIG. 3a depicts human skin after cleansing with the present invention and is magnified (about 3×).
Figure 3B:
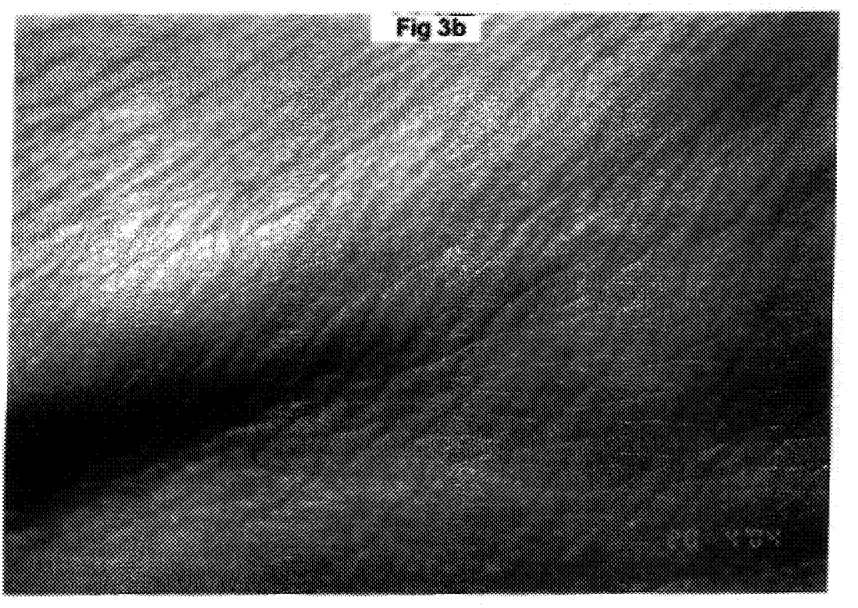
FIG. 3b depicts human skin after cleansing with the present invention and is magnified (about 3×).
Figure 4A:
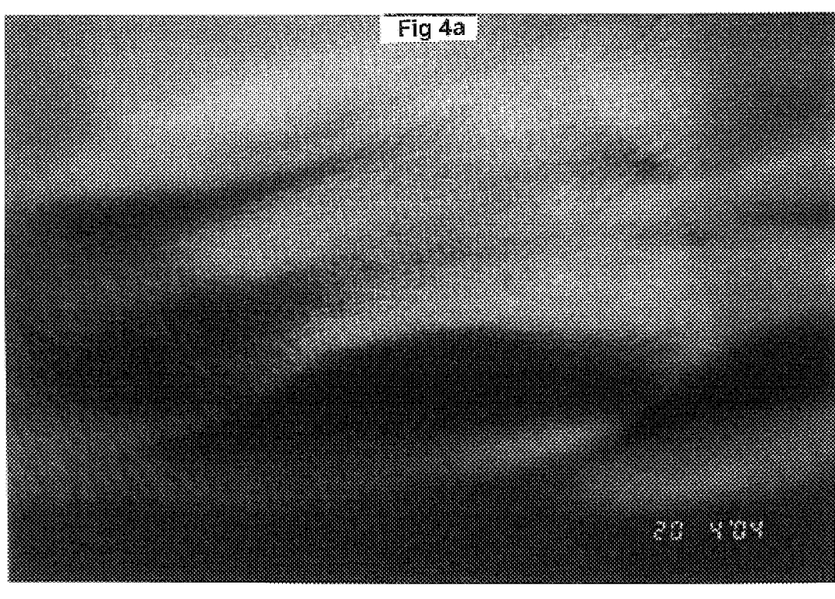
FIG. 4a depicts the same magnified human skin after cleansing as FIG. 3a, but was photographed under ultraviolet light.
Figure 4B:
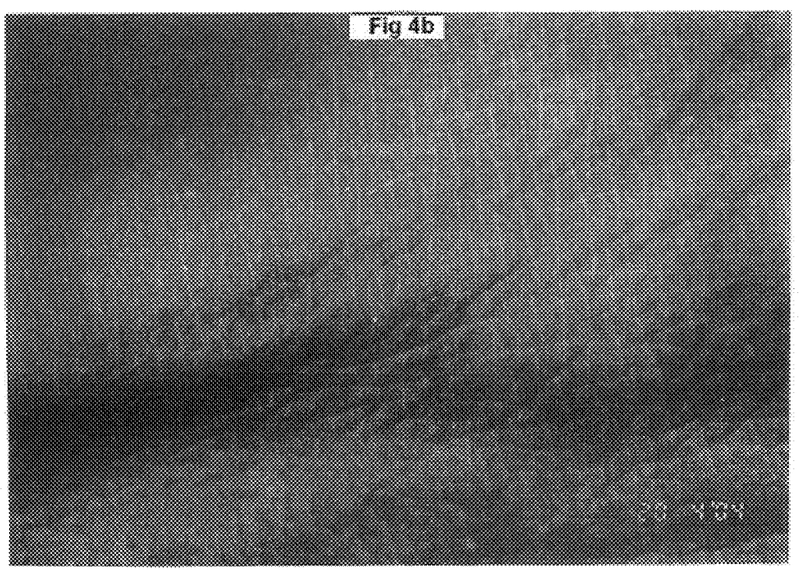
FIG. 4b depicts the same magnified human skin after cleansing as FIG. 3b, but was photographed under ultraviolet light.

FIGS. 3a, 3b, 4a, and 4b are all "after cleansing" photos of the back of the hand. As seen in FIGS. 3a and 3b, the furrows appear clean and indicate penetration into the crevices of the skin and good cleansing. The yellow fluorescent dots in most furrows of FIGS. 4a and 4b also indicate excellent deposition and retention of the present invention.

EXAMPLE 3

The composition set forth in Table 5 was formulated as follows. When possible all reaction vessels were covered to reduce water loss due to evaporation in the following process. The sodium methyl oleyltaurate was heated to about 60-65° C. for at least about 12 hours before dispensing. First, the sodium methyl oleyltaurate and disodium oleamido MEA sulfosuccinate were mixed at 300 rpm for about 15 minutes. Then, the mixture was heated to about 70-75° C. while stirring at 300 rpm. Then propylene glycol (and) PEG-55 propylene glycol oleate; sodium lauryl sulfoacetate (and) disodium laureth sulfosuccinate, and sodium cocoyl isethionate were added in order and mixed for 15 more minutes and maintained at about 70-75° C. This was the "First Mixture."

Then, in a separate tank, the initial water amount (which is about 37% of the total water used in Example 2) was added (and water was purged with nitrogen for at least two hours) and then glycerin was added and mixed at about 26 rpm and heated to about 70-75° C. for about 14-25 minutes. Then the combination was mixed and heated to 70° C. for about 9 to about 50 minutes. One of ordinary skill in the art would understand that the rpm and mixing times will vary according the batch size, and dissolution of the ingredients. Then the methyl paraben and propyl paraben is added while mixing and maintaining about 70° C. and mixing for about 6 to 22 minutes. It may be preferable to take some mixture off the bottom and add to the top until all materials are completely dissolved. The edetate disodium and allantoin were added while maintaining about 70° C. and mixing at about 15 rpm for about 10 minutes. This mixture was in the "Main Tank." The mixture that resided in the Main Tank is the "Second Mixture."

The First Mixture was added to the Main Tank while mixing at about 60 rpm for about 8 to 18 minutes. This addition occurred slowly to avoid foaming. The combined mixture is then mixed for about an additional 15 minutes at about 15 rpm and at about 70-75° C.

In another tank, cetyl alcohol and stearyl alcohol were mixed at about 225 rpm and about 70-75° C. for about 30 minutes to about 1 hour 29 minutes. While mixing, sorbitan monoleate, glyceryl stearate (and) PEG-100 stearate, butylated hydroxytoluene and alpha-bisabolol were added in order, allowing for complete liquefaction after each addition. This was the "Third Mixture." Then the Third Mixture was added to the Main Tank slowly to avoid foaming and mixed for about 15 more minutes at about 15 rpm and about 70-75° C.

Then, water (about 26.1% of the total water used in Example 2) was placed in a separate tank and purged with nitrogen for at least about 2 hours. Then the tank was heated to about 60-65° C. Sulfur was added and homogenized for 15 minutes to get a smooth suspension. After rinsing the homogenizer with water and removing it, a mixer was used at about 300 rpm. Sodium methyl oleyltaurate was then added and mixed for about 10 minutes. PEG-150 pentaerythrityl tetrasterate was added and mixed until the composition was uniform. 60-65° C. was the approximate temperature and mixing occurred for approximately another 15 minutes until the composition was uniform. This was the "Fourth Mixture."

The Fourth Mixture was added to the Main Tank and a vacuum of about −0.8 to −0.6 bar was again pulled. The Main Tank was mixed for not less than about 15 minutes at about 15 rpm and about 70-75° C. Then, the Main Tank was cooled to about 37-40° C. to achieve homogeneity.

In a separate vessel, water (about 1.9% of the total water used in Example 2) was purged with nitrogen for at least about 2 hours and mixed at about 400 rpm and about 60-65° C. while edetate sodium was added. Mixing occurred until materials were completely dissolved and then the vessel was cooled to about 35-40° C. Aloe vera gel was then added and then mixed to get a clear homogeneous solution, while about 35-40° C. was maintained. This was the "Fifth Mixture." The Fifth Mixture was then added to the Main Tank. A vacuum of about −0.8 to −0.6 bar was drawn and maintained for at least about 15 minutes. The mixing speed was about 18 rpm and the temperature was about 35-40° C.

In a separate vessel, water (about 29% of the total water used in Example 2) was purged with nitrogen for at least about 2 hours. The nitrogen blanket was maintained for the following additions, while there was mixing at about 225 rpm and heating to about 35-40° C. The following were added in order, allowing for complete dissolution after each addition: sodium thiosulfate and sulfacetamide sodium. This was the "Sixth Mixture." Then, the Sixth Mixture was added to the Main Tank under vacuum (about −0.8 to −0.6 bar) and mixed at about 26 rpm and then the Main Tank was cooled to about 30 to 35° C.

Fragrance was then added and mixed for about 15 minutes at about 26 rpm. Vacuum was drawn to about −0.8 to −0.6 bar and the Main Tank was mixed for about 1 hour. Then it was cooled to about 25 to 30° C.

The vacuum was broken and water (about 5.8% of the total water used in Example 2), which had been purged with nitrogen for at least 2 hours, was added. Vacuum of about −0.8 to −0.6 bar was drawn and mixing occurred for about 1 hour at about 26 rpm.

This embodiment was then packaged in plastic jars which had been flooded with nitrogen, or poly-lined fiber drums with LDPE bags, which had been flooded with nitrogen. Later, this composition was applied to non-woven cloth.

EXAMPLE 4

One batch of the present invention as described in Table 5 and Example 3 was prepared, except that the additional 3% water was not added a processing aid, deposited on a non-woven cloth, sealed in a package and tested for stability.

The composition on the cloth was tested initially and after being stored at about 25° C., about 60% relative humidity and at about 40° C., about 70% relative humidity for 1, 2 and 3 months. Additionally, the compositions were visually observed for discoloration, which is also a sign of degradation, and is not cosmetically acceptable.

TABLE 9

|  | Initial | 1 month 25° C./60% | 1 month 40° C./75% | 2 month 25° C./60% |
|---|---|---|---|---|
| Sulfacetamide (mg/cloth) | 422.6 | 419.2 | 408.0 | 411.5 |
| % RSD (n = 3) | 5.4 | 9.7 | 5.1 | 6.5 |
| Sulfanilamide (% w/w) | 0.69 | 1.11 | 2.74 | 1.68 |
| % RSD (n = 3) | 3.02 | 1.75 | 1.53 | 10.84 |
| Sulfur (mg/cloth) | 201.9 | 208.4 | 207.5 | 203.3 |
| % RSD (n = 3) | 4.4 | 10.4 | 6.9 | 8.49 |

TABLE 9-continued

| Appearance | Yellow cloth No discoloration | Yellow cloth No discoloration | Yellow cloth No discoloration | Yellow cloth No discoloration |
|---|---|---|---|---|
|  | | 2 month 40° C./75% | 3 month 25° C./60% | 3 month 40° C./75% |
| Sulfacetamide (mg/cloth) | | 379.0 | 419.2 | 360.0 |
| % RSD (n = 3) | | 2.9 | 6.6 | 3.7 |
| Sulfanilamide (% w/w) | | 5.46 | 1.97 | 7.12 |
| % RSD (n = 3) | | 10.3 | 0.88 | 9.41 |
| Sulfur (mg/cloth) | | 194.5 | 207.26 | 204.32 |
| % RSD (n = 3) | | 3.76 | 0.74 | 1.12 |
| Appearance | | Yellow cloth No discoloration | Yellow cloth No discoloration | Yellow cloth No discoloration |

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

We claim:

1. A skin treatment composition for the treatment of skin disorders comprising
    water at about 48.66%,
    glycerin at about 2%,
    methyl paraben at about 0.15%,
    propyl paraben at about 0.05%,
    allantoin at about 0.10%,
    sodium methyl oleyltaurate at about 9.15%,
    disodium oleamido MEA sulfosuccinate at about 3.85,
    sodium cocoyl isethionate at about 6.50%,
    sodium lauryl sulfoacetate (and) disodium laureth sulfocinate at about 4.50%,
    cetyl alcohol at about 1.00%,
    stearyl alcohol at about 1.50%,
    sorbitan monooleate at about 2.00%,
    glyceryl stearate (and) PEG 100 stearate at about 2.00%,
    butylated hydroxytoluene at about 0.15%,
    alpha bisabolol natural at about 0.10%,
    precipitated sulfur at about 5.00%,
    propylene glycol (and) PEG-55 propylene Glycol Oleate at about 1.35%,
    PEG-150 pentaerythrityl tetrastearate at about 0.15%,
    edetate disodium at about 0.20%,
    aloe vera gel at about 0.10%,
    sodium thiosulfate at about 0.15%, and sulfacetamide sodium at about 11.24%, wherein the skin disorder is selected from the group consisting of acne vulgaris, acne rosacea and seborrheic dermatitis.

2. The composition of claim 1 further comprising an additional about 3.00% water.

\* \* \* \* \*